US00PP26685P3

(12) United States Plant Patent
Jury

(10) Patent No.: US PP26,685 P3
(45) Date of Patent: May 3, 2016

(54) ***MAGNOLIA* PLANT NAMED 'JURMAG5'**

(50) Latin Name: ***Magnolia* hybrid**
Varietal Denomination: Jurmag5

(71) Applicant: Mark Jury, Waitara (NZ)

(72) Inventor: Mark Jury, Waitara (NZ)

( * ) Notice: Subject to any disclaimer, the term of this patent is extended or adjusted under 35 U.S.C. 154(b) by 235 days.

(21) Appl. No.: 13/998,945

(22) Filed: Dec. 20, 2013

(65) Prior Publication Data

US 2015/0181788 P1 Jun. 25, 2015

(51) Int. Cl.
*A01H 5/00* (2006.01)

(52) U.S. Cl.
USPC ..... Plt./223

(58) Field of Classification Search
USPC ..... Plt./223, 216
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Magnolia* cultivar named 'JURMAG5' is disclosed, characterized by having a compact habit, slower growth and large yellow-orange flowers with distinctly rounded petals. The new variety is a *Magnolia,* normally produced as an ornamental plant.

2 Drawing Sheets

Figure 1:
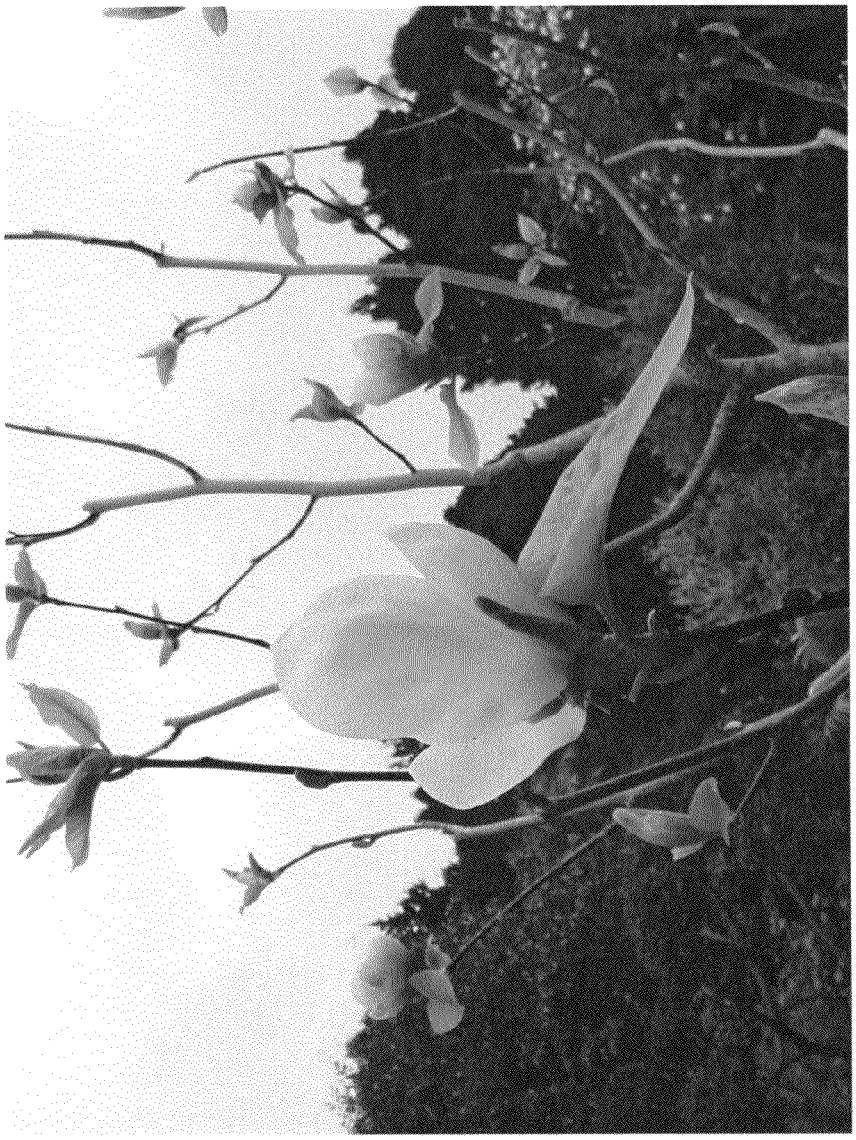

Latin name of the genus and species: *Magnolia* hybrid.
Variety denomination: 'JURMAG5'.

BACKGROUND OF THE INVENTION

The new cultivar is a product of a planned breeding program. The new variety resulted from a crossing performed in 1993 in North Taranaki, Nth Is, New Zealand. The seed parent is the unpatented variety, *Magnolia accuminata* 'Yellow Bird'. The pollen parent is the unpatented variety *Magnolia* hybrid 'Iolanthe'. The new variety was selected 2002, by the inventor, Mark Jury at Waitara, North Taranaki, Nth Is, New Zealand in a group of seedlings resulting from the 1993 crossing.

Asexual reproduction of the new cultivar 'JURMAG5' by vegetative cuttings was first performed at a commercial nursery in New Zealand during 2002 and has shown that the unique features of this cultivar are stable and reproduced true to type on successive generations.

SUMMARY OF THE INVENTION

The cultivar 'JURMAG5' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'JURMAG5' These characteristics in combination distinguish 'JURMAG5' as a new and distinct *Magnolia* cultivar:

1. Compact growth habit.
2. Yellow-Orange colored petals.
3. Growth habit less vigorous than other yellow flowering *Magnolias.*
4. Distinctive rounded petals.
5. Large flower size.

PARENT COMPARISON

Plants of the new cultivar 'JURMAG5' are similar to plants of the seed parent, *Magnolia* 'Yellow Bird' in most horticultural characteristics, however, plants of the new cultivar 'JURMAG5' have significantly larger flowers than the seed parent variety.

Plants of the new cultivar 'JURMAG5' are similar to plants of the pollen parent, *Magnolia* 'Iolanthe' in most horticultural characteristics, however, plants of the new cultivar 'JURMAG5' have creamy yellow flowers, whereas the pollen parent variety has pink and white flowers.

Plants of the new cultivar 'JURMAG5' are similar to plants of the commercial variety, *Magnolia acuminata* 'Butterflies', unpatented in most horticultural characteristics, however, plants of the new cultivar 'JURMAG5' differ in the following:

1. Flowers of the new variety are Yellow-Orange, whereas flowers of 'Butterflies' are yellow.
2. Flowers of the new variety open fully, whereas flowers of 'Butterlies' stay tightly held together.
3. Plants of the new variety are more compact in growth habit.
4. Petals of the new variety are broader and more rounded than petals of 'Butterflies'.

Plants of the new cultivar 'JURMAG5' are similar to plants of the commercial variety, *Magnolia* hybrid 'Elizabeth', unpatented in most horticultural characteristics, however, plants of the new cultivar 'JURMAG5' differ in the following:

1. Flowers of the new variety are Yellow-Orange, whereas flowers of 'Elizabeth' are light Yellow with Green-Yellow petal bases.
2. Flowers of the new variety are approximately 5 inches in diameter, whereas flowers of 'Elizabeth' are approximately 3 inches in diameter.
3. Plants of the new variety are much more compact and less vigorous in growth habit.

BRIEF DESCRIPTION OF THE PHOTOGRAPHS

The accompanying photograph in FIG. 1 illustrates in full color a typical young flowers of 'JURMAG5' outdoors.

Figure 2:
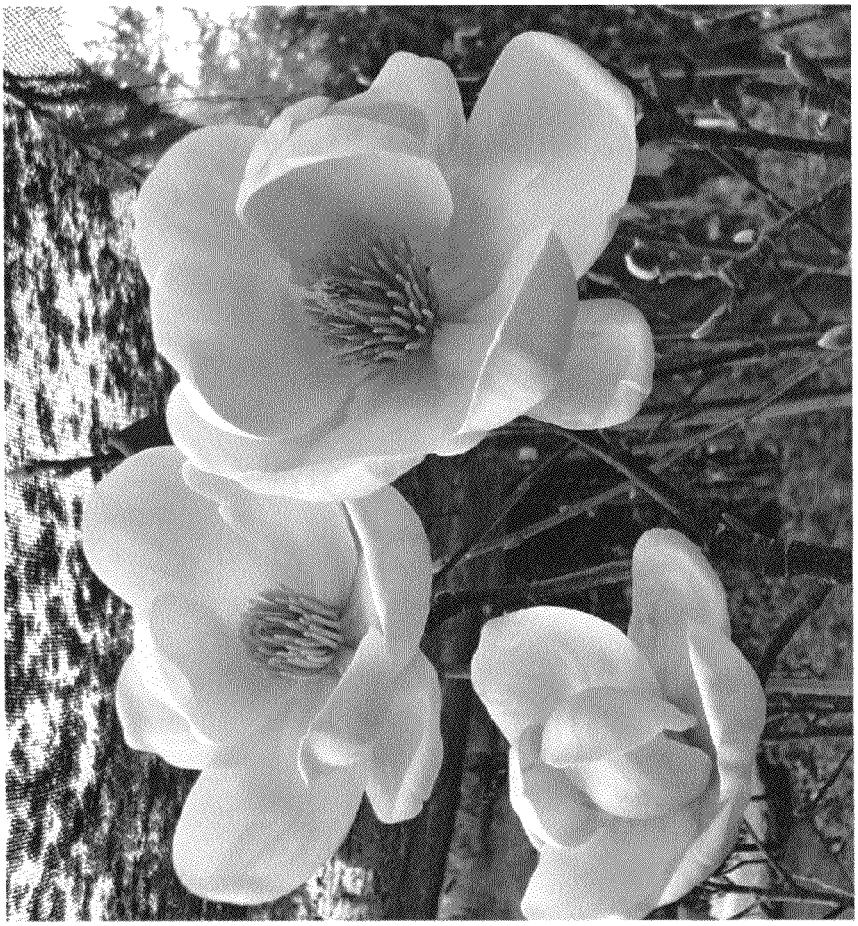

FIG. 2 illustrates in full color typical mature flowers of 'JURMAG5'.

Age of the plant producing the flowers is approximately 20 years. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'JURMAG5' plants grown outdoors in New Zealand. Growing conditions are similar to USDA zone 7. Measurements and numerical values represent averages of typical plant types.

Botanical classification: *Magnolia* hybrid 'JURMAG5.'

PROPAGATION

Time to initiate roots: About 60 days at approximately 21° C.
Time to produce a rooted cutting: About 120 days at 21° C.
Root description: Typical *Magnolia* root, thick, coarse, and white.

PLANT

Growth habit: Compact, upright tree.
Age of plant described: 20 years.
In a container or in the ground: Ground.
Height: Approximately 4 meters.
Plant spread: Approximately 3 meters.
Growth rate: Slow to average.
Length of primary lateral branches: Approximately 50 cm.
Diameter of lateral branches: Aproximately 15 cm.
Quantity of lateral branches: Approximately 20.
Branching arrangement: Sub-opposite.
Trunk:
- *Diameter.*—Approximately 18 cm, after 20 years. Measured at approximately 10 cm above soil level.
- *Texture.*—Smooth.
- *Color.*—Near RHS Greyed-Green 189C.

FOLIAGE

Leaf:
- *Arrangement.*—Alternate.
- *Quantity.*—Approximately 8 per main branch.
- *Average length.*—Approximately 20 cm.
- *Average width.*—Approximately 13 cm.
- *Shape of blade.*—Ovate.
- *Apex.*—Acuminate.
- *Base.*—Cuneate.
- *Margin.*—Entire.
- *Texture of top surface.*—Smooth.
- *Texture of bottom surface.*—Moderately pubescent.
- *Pubescence.*—Moderate, present only on underside.
- *Leaf internode length.*—Approximately 3 cm.
- *Color.*—Young, foliage upper side: Near RHS Green 139D. Young foliage under side: Near RHS Green 139D. Mature foliage upper side: Near RHS Green 137A. Mature foliage under side: Near RHS Green 143A.
- *Venation.*—Type: Pinnate. Venation color upper side: Near RHS Green 137B. Venation color under side: Near RHS Green 143B.
- *Petiole.*—Average Length: Approximately 1.5 cm. Color: Near RHS Green 141B. Diameter: Approximately 3 cm.

FLOWER

Natural flowering season: August through September, in the Southern hemisphere.
Begins flowering after how many years/months: 1 year from bud stage.
Inflorescence type and habit: Singly occurring, overlapping cupping, flowers.
Rate of flower opening: Approximately 6 days from bud to fully opened flower.
Flower longevity on plant: 4 to 5 days, after fully opened.
Quantity of flowers: Approximately 50 open flowers per tree.
Flower size:
- *Diameter.*—Approximately 12 cm.
- *Height.*—Approximately 8 cm.

Pedicel:
- *Length.*—1 cm.
- *Diameter.*—0.8 cm.
- *Color.*—Near RHS Yellow-Green 144C.

Petals:
- *Petal arrangement.*—Whorled, overlapping.
- *Size.*—Length: Range from approximately 5.0 cm to 8.0 cm. Width: Range from approximately 5.0 cm to 8.0 cm.
- *Margin.*—Entire.
- *Apex.*—Rounded.
- *Petal quantity.*—12.
- *Texture.*—Smooth.

Color:
- *Petals.*—When opening: Upper surface: Near RHS Yellow-Orange 18D. Lower surface: Near RHS Yellow-Orange 18D. Fully opened: Upper surface: Near RHS Yellow-Orange 18C. Lower surface: Near RHS Yellow-Orange 18C.

Bud:
- *Shape.*—Ovate.
- *Length.*—Approximately 5 cm.
- *Diameter.*—Approximately 2 cm.
- *Color.*—Near RHS Yellow 11 D.

Sepals/tepals:
- *Shape.*—Lanceolate.
- *Quantity.*—12.
- *Length.*—Approximately 1 cm.
- *Width.*—Approximately 0.5 cm.
- *Margin.*—Entire.
- *Texture.*—Smooth.
- *Fragrance.*—Moderate, slightly lemony.

REPRODUCTIVE ORGANS

Stamens:
- *Number.*—Approximately 35.
- *Filament length.*—Approximately 1.5 cm.
- *Filament color.*—Near RHS Yellow 10A.

Anthers:
- *Length.*—Approximately 0.7 cm.
- *Shape.*—Linear.
- *Color.*—Colored by moderately produced pollen, Yellow-range 20A.

Pistil:
- *Number.*—1.
- *Length.*—Approximately 1.5 cm.

*Style.*—Length: Approximately 1.4 cm. Color: Near RHS Yellow 2C.

OTHER CHARACTERISTICS

Seeds and fruits: The new cultivar does not set seed. Female sterile.

Disease/pest resistance: Neither resistance nor susceptibility to pathogens and pests common to *Magnolia* have been observed.

Temperature tolerance: The new variety is suitable for growing in USDA zones 3 through 8.

What is claimed is:

1. A new and distinct cultivar of *Magnolia* plant named 'JURMAG5' as herein illustrated and described.

* * * * *